March 29, 1955 J. D. BROWNELL Plant Pat. 1,371
ROSE PLANT
Filed April 12, 1954
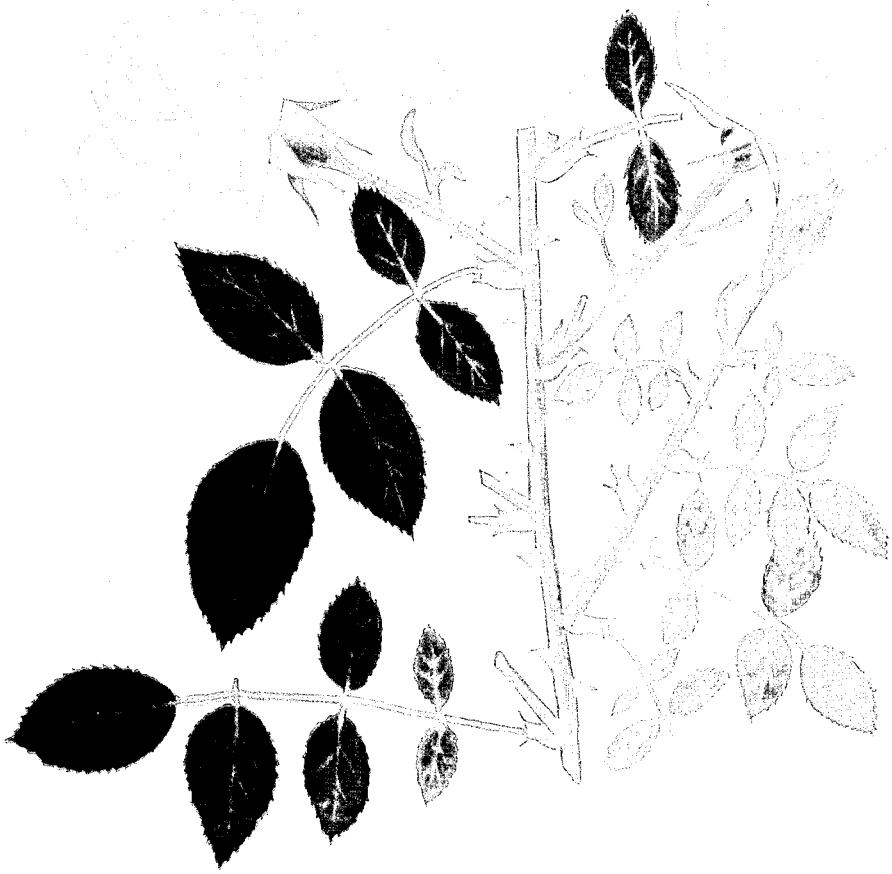
INVENTOR.
Josephine D. Brownell.

United States Patent Office

Plant Pat. 1,371

Patented Mar. 29, 1955

1,371

ROSE PLANT

Josephine D. Brownell, Little Compton, R. I.

Application April 12, 1954, Serial No. 422,710

1 Claim. (Cl. 47—61)

My invention relates to roses and especially to a new, original and distinct variety of the class known commercially as "hybrid teas" and is a variant in that class, being a *Rosa wichuraiana* hybrid tea hybrid, produced by me and under my direction in the breeding grounds of my research gardens in Little Compton, Rhode Island, by cross pollenation, which can be and has been asexually reproduced.

My new rose is new as to the following characteristics and especially as to their joint association with the characteristics inherited from *Rosa wichuraiana*, of hardiness, or immunity from serious injury on account of cold temperatures prevailing in certain parts of the northern United States;

The light to dark pink shades (ordinary dictionary definition) of its petals, in combination with the unique brilliance thereof and their tendency to hold these colors under exposure;

The notable resistance to blackspot;

The novelty and variation within certain definite limits of the form of the bloom, its character of holding that form for a long time and the petallage of the flowers;

Its character of fragrance;

Its unusual abundance of flowers, at bloom time and after early bloom time and until frost;

The intensity of its remontant and everblooming or reblooming character;

Its character of ascending in height by recurrent branching and progressively longer stems.

The character of producing many seven leafleted leaves; which character seldom has obtained on hybrid teas not having *Rosa wichuraiana* ancestry, but frequently obtains on flower stems of descendants of *Rosa wichuraiana* of the dwarf reblooming type;

And especially its characteristic of freedom from premature defoliation by black-spot, under certain definite conditions of exposure, without any cultural control.

In the accompanying drawing forming a part of this specification I have shown my new rose in its natural colors, that is, as near as is possible to do so artificially.

My new rose is otherwise described as follows:

ESSENTIAL INFORMATION

*Type*

Hybrid tea, *Rosa wichuraiana* hybrid, dwarf to ascending up to four feet in height, for garden display, cut flower and forcing or growing under glass.

*Class*

Hybrid tea crossed with *Rosa wichuraiana,* further restricted by originator to include only those varieties that can survive moderately low sub-zero temperatures.

*Breeding*

This variety was produced and bred by me and under my direction by propagation and cross pollenation.

It came into being as a seedling between "Free Gold," not patented, as pollen parent and "Curly Pink," Plant Patent No. 842, as seed parent.

The plant and flower seemed to me to be of unusual merit and I have since made and directed extensive propagations and tests thereof.

Plants of this variety budded from this seedling on to *Rosa multiflora* root stock, have after being exposed to moderate sub-zero temperatures, survived and bloomed normally the following season in the hybrid tea manner.

The variety has been propagated by budding at Little Compton, Rhode Island, in the months of July and August in 1950 and 1951, inclusive and the characters have successively reproduced, true to the original seedling.

FLOWER

*Habit*

It blooms out of doors in Little Compton, beginning about three days prior to the average beginning time of commercial hybrid teas and continues relative to growth of the plant until frost.

*Flowers borne*

Often one and frequently two or three or more on each stem in the usual hybrid and floribunda tea type of cluster. The pedicels and peduncles are medium in diameter and medium in length, erect, stiff, smooth, free from prickles and bristles. Stems are long, diameter medium and notably stiff and rigid.

*Quantity of bloom*

Free, being cumulative in quantity from year to year as the plant increases in size, flowering through the summer.

*Fragrance*

Distinctive, pleasing china tea in combination with that of *Rosa wichuraiana*, under favorable environment.

*Bud*

Neck normal as described, opens well, being little to not at all affected by hot or wet weather or both, as to color and form, except at very high temperatures the color is less intense and the form of the petals is less recurled.

Before the calyx breaks the size is medium, form moderately pointed, frequently with one or more sepals having foliaceous parts extending beyond the apex of the calyx up to about one half of an inch, the number and size of the foliaceous parts being variable, otherwise the sepals are usually normal and regular, tapering to lanceolate at their apex, turning back nearly perpendicular to the pedicel as the bud opens.

Color of the bud as the calyx opens; outside of petals top Rose Opal at o22, this reference and the following except as otherwise noted is to British Horticultural Color Chart, shading down to nearly Neyron Rose at 623/1.

*Bloom*

As the bud opens inside of petals Rose Opal at o22/1 shading toward base to Azalea Pink at 618/1, with slight overlay at extreme base of Chrome Yellow at 605/2; outside of petals, Azalea Pink at 618, with markings at extreme base of Chrome Yellow at 605/2, and as the flower develops to maturity the colors slowly soften to China Rose at o24/3 maintaining for an unusually long time the colors above described.

The flower usually varies in size from three to four inches in diameter when fully open, petals average between 60 and 75, frequently some smaller petals and petalloids in the center, variable in number.

The flower opens high centered to ovoid, nearly informal, slightly recurled. The petals are variable from obovate to ovate to irregular and frequently with surfaces of the smaller petals notably irregular. Texture is medium thick, both sides brilliant. The time of opening in favorable conditions is four to six days.

The petals are substantial and after about five to six days drop off cleanly, except that occasionally one or two inner petals or petaloids cling to turn dull, to fall later. The flower does not "ball" in wet weather. The flower lasts well, is not affected at any stage by moderate cold or hot temperatures, or by humidity or wet weather.

*Productive organs*

Stamens, quantity variable none to few, of slightly uneven length.

Anthers, Burnt Orange o14/3. Filaments, nearly Maize Yellow at 607/1.

Pistils are several of slightly uneven lengths, averaging around one-half inch long.

Ovaries are usually all inclosed.

Hips frequently develop to ovoid to globular, color comparable with that of leaves with variable colored overlay on the side exposed to the sun, moderately smooth; walls, thin, fleshy, medium in size.

Sepals are persistent and break off easily.

PLANT

*Foliage*

Is abundant, of compound leaves of three to five leaflets near the flower, five leaflets lower down the stem and frequently seven leaflets in the middle of the stem and nearer the base and occasionally between cluster stems. Size of leaflets medium, averaging in size about half way between the average hybrid tea and the *Rosa wichuraiana* leaflets. As the plants develop in size some of the leaflets develop to one half larger than the size described above. Form of leaflets usually ovate with apex slightly acute, base rounded, margins with small pointed serrations, petiolules short.

The leaflets average in width about two-thirds of their length. They are notably irregularly variable in size.

Color references hereinafter are to Robert Ridgway Color Standard.

Color of leaflets on the upper surface is slightly variable from Dark Dull Yellow Green, with reverse side nearly Asphodel Green.

The rachises are medium, moderately narrow to slender, upper side smooth except some very short hairs on edges almost microscopic. Under side moderately smooth, usually 3 to 5 short prickles.

Stipules are medium, averaging about one-half to three-fourths of an inch long and somewhat wider than normal with sharp points narrower than usual, the upper edges of which normally form an angle of about 60 degrees.

Habit, dwarf, becoming bushy to tall up to four feet in three years and under favorable vegetative opportunity occasionally up to five feet in four years; upright, compact, more cumulative in growth from year to year than the normal hybrid tea rose plant, by stems from the base and by rebranching and growth and enlargement and extension of the stems from the base. The growth is moderately free at first, developing more rapidly after one or two years under favorable vegetative opportunity.

A notable difference from most rose plants is in the manner of growth of the stems. The leaves being closer together on the stems more eyes than normal are produced and more stems grow therefrom, with open clusters in some cases with ten or more cluster stems, thus increasing the production of blooms.

Color of mature stems is the same as that of the upper surface of mature leaves, shading variously lighter.

Prickles, several, frequently two to four between leaves, averaging in length about one-quarter inch, shading from Chrysanthemum Crimson to lighter, turning lighter throughout and later to nearly colorless.

*Winter resistance*

A notable characteristic of this new rose is the resistance to moderate sub-zero temperatures in combination with its hybrid tea character and its *Rosa wichuraiana* ancestry. This variety with grafted bud and plant above that bud entirely exposed above ground to moderate sub-zero temperatures survived and bloomed normally the following season. The word temperature herein refers to the Fahrenheit scale.

In comparison with other Sub Zero hybrid teas, being *Rosa wichuraiana* hybrids.

"Pink Princess," Plant Patent No. 459, is a taller growing variety, the blooms are larger with less petals and more high centered. "Sun Up," Plant Patent No. 1,015, is a larger flower and is not free from blackspot as is my new rose.

I claim:

The rose plant variety substantially as shown and described, characterized by its unique color, form, arrangement, bloom cluster and resistance to moderate sub-zero temperatures and to blackspot.

No references cited.